(12) United States Patent
Mehravaran

(10) Patent No.: US 12,364,392 B2
(45) Date of Patent: Jul. 22, 2025

(54) METHOD AND DEVICE FOR FELLOW-EYE CORNEAL TOPOGRAPHY

(71) Applicant: Morgan State University, Baltimore, MD (US)

(72) Inventor: Shiva Mehravaran, Nottingham, MD (US)

(73) Assignee: Morgan State University, Baltimore, MD (US)

( * ) Notice: Subject to any disclaimer, the term of this patent is extended or adjusted under 35 U.S.C. 154(b) by 442 days.

(21) Appl. No.: 18/060,233

(22) Filed: Nov. 30, 2022

(65) Prior Publication Data

US 2024/0074654 A1 Mar. 7, 2024

Related U.S. Application Data

(60) Provisional application No. 63/404,064, filed on Sep. 6, 2022.

(51) Int. Cl.
*A61B 3/107* (2006.01)
*A61B 3/00* (2006.01)
*A61B 3/10* (2006.01)

(52) U.S. Cl.
CPC ............ *A61B 3/107* (2013.01); *A61B 3/0025* (2013.01); *A61B 3/102* (2013.01)

(58) Field of Classification Search
CPC ......... A61B 3/0025; A61B 3/13; A61B 3/102; A61B 3/107; A61B 3/117
See application file for complete search history.

*Primary Examiner* — Jack Dinh
(74) *Attorney, Agent, or Firm* — Whiteford, Taylor & Preston, LLP; Peter J. Davis

(57) ABSTRACT

A device and method for early detection of eye disease including a corneal topography device including a camera, such as a rotating Scheimpflug camera, configured to measure the elevation of a patient's two anterior corneas sequentially or simultaneously; a computer processor; and non-transitory computer readable media including computer readable instructions, which, when executed by the computer processor, causes the device to measure and store elevation data at a plurality of points on the patient's anterior corneal surfaces; organize the elevation data for each cornea into a two-dimensional matrix where the center of the cornea is in the center of the data frame, rotate the data for a first eye 180 degrees around the Y axis relative to a second eye, subtract data on each corresponding corneal point, and generate an elevation difference matrix showing the degree of symmetry or asymmetry between the patient's left and right eye corneal topography.

4 Claims, 5 Drawing Sheets

Figure 3

METHOD AND DEVICE FOR FELLOW-EYE CORNEAL TOPOGRAPHY

BACKGROUND OF THE INVENTION

Field of the Invention

The present invention relates to corneal imaging.

Description of the Background

Looking at the anatomy of the human eye, the front third is known as the anterior segment and includes the cornea which is aspheric in shape (FIG. 1). Light enters the globe through the cornea, which is a clear tissue with no blood vessels. The cornea contributes about two thirds of the focusing power of the eye. The cornea is about 10-12 mm in diameter and approximately 500 microns thick.

Some of the main corneal parameters measured by modern ocular imaging systems are curvature, elevation, and thickness. The patterns observed with each of these parameters can be classified into different categories. For example, the normal patterns of axial curvature include round, oval, and symmetric bowtie. Irregular patterns are usually due to corneal pathological conditions, previous surgery, or trauma.

Corneal ectatic disorders or corneal ectasia are a group of eye disorders, including keratoconus, pellucid marginal degeneration, and post-surgical ectasia, characterized by corneal thinning and steepening. While advanced cases of keratoconus (thickness <400 microns and curvature >53 diopters) are easily identified on slit-lamp and topographic examinations, early stages of the disease can go undiagnosed and lead to severe post-surgical ectasia.

Modern computerized corneal topography machines generate very large amounts of data that are used for the diagnosis and treatment follow-up of different corneal conditions, as well as screening before refractive surgery. Today, there are a variety of state-of-the-art computerized corneal topographers available that can provide large amounts of data and a 3-D representation of the anterior segment of the eye. One example is the OCULUS Pentacam (Wetzlar, Germany), which utilizes a rotating Scheimpflug camera to generate images of the anterior segment. Pentacam directly measures the height data (elevation) of both the anterior and posterior cornea (FIG. 2). It then processes elevation data along several points on the anterior and posterior surfaces. This data is then converted into anterior and posterior curvature in diopters as well as corneal thickness or pachymetry in microns. All images are digitized, and a 3D model of the anterior segment is calculated from as many as 25,000 (HR: 138.000) distinct elevation points. The system also uses the data to compute a number of diagnostic indices whose normal ranges are based on a sample population.

Despite remarkable advances in corneal topography, identifying early subclinical stages of progressive corneal degenerative diseases and detecting subtle corneal abnormalities remain a challenge. A major limitation is that imaging and diagnosis is performed for one eye independent of the fellow eye, by comparing it to population-based reference ranges which vary substantially by the demographic composition of the population. Research has shown that the cornea is thinner in younger age, females, Black/African Americans, and diabetics. As such, using reference ranges derived from nonrepresentative populations (e.g., white populations) can lead to misdiagnosis and consequent health disparities. Furthermore, evaluation of topography using currently available metrics and indices can be very subjective and dependent on clinician expertise, especially in borderline and suspect cases, and the sensitivity and specificity of diagnostic algorithms still need to be improved. This unmet needs places two major groups of patients at risk: 1) The millions of patients who seek surgical correction (e.g., LASIK) for their refractive errors (the most common cause of visual impairment in the US and worldwide) and rely on sensitive and specific screening criteria to avoid postoperative complications, and 2) Patients with corneal ectasia and degenerative diseases such as keratoconus. In these patients, delayed or missed diagnosis significantly reduces the long-term prognosis and may lead to severely impaired vision and quality of life.

SUMMARY OF THE INVENTION

The present invention is a corneal topography device and integrated software that effectively measures the point-by-point difference between corneal topographies of both of a patient's eyes and digitally overlays them to detect asymmetry between the patient's corneal topography.

Accordingly, there is provided according to the invention a device comprising a rotating Scheimpflug camera configured to measure the elevation of a patient's two corneas sequentially; a computer processor; and non-transitory computer readable media including computer readable instructions, which, when executed by the computer processor, causes the device to measure and store elevation data at a plurality of points on the patient's anterior corneal surfaces; organize the elevation data for each cornea into a two-dimensional matrix where the center of the cornea is in the center of the data frame, rotate the data for a first eye 180 degrees around the Y axis relative to the fellow (contralateral) eye, subtract data on each corresponding corneal point, and generate an elevation difference matrix and colormaps whose patterns have been named and described for the first time by the inventor.

There is further provided according to the invention a method for early detection of eye disease comprising the steps: using a corneal topography device and integrated software to measure and store elevation data at a plurality of points on the patient's anterior corneal surfaces; organize the elevation data for each cornea into a two-dimensional matrix where the center of the cornea is in the center of the data frame, rotate the data for a first eye 180 degrees around the Y axis relative to a second eye, subtract data on each corresponding corneal point, and generate summary indices from the elevation difference matrix showing the degree of symmetry or asymmetry between the patient's left and right eye corneal topographies that are used to label the patient with a diagnostic category (e.g. normal, keratoconus suspect, advanced keratoconus, aniso-astigmatism). The diagnostic categories may be improved and refined using machine learning clustering applied to collected data.

BRIEF DESCRIPTION OF THE DRAWINGS

The foregoing summary, as well as the following detailed description of the preferred invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown. In the drawings:

FIG. 3 shows an example of a raw data file, that has been converted to a MS Excel sheet, containing corneal elevation data of a portion of a single eye.

DETAILED DESCRIPTION OF THE INVENTION

Normal corneas are highly symmetric and therefore interocular asymmetry may be used to detect abnormality. The invention compares fellow eye data (difference between thousands of corresponding points on the cornea) and provides metrics to assess the level of symmetry and patterns of asymmetry between fellow eyes and identify cases with subtle abnormalities that would appear normal if examined individually compared to commonly used references. As an example, the invention may be used to detect ectasia at its very early stages (before it has clinical signs or symptoms) so that patients can receive proper treatment in a timely manner and do not undergo any surgical procedures (e.g. LASIK and PRK) which can make their condition worse.

Figure 1:
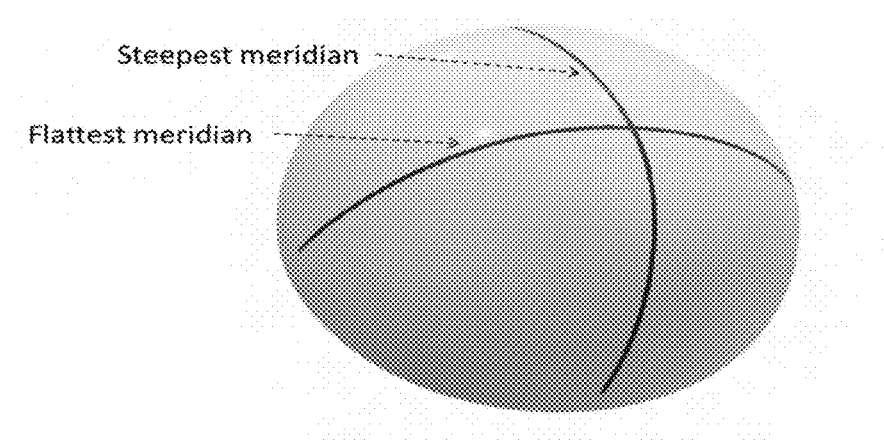
FIG. 1 shows the aspheric shape of the cornea. This is commonly described using the flattest and steepest meridians which are measured as the minimum and maximum keratometry readings, respectively. The difference between the refractive powers in these two main meridians is a measure of corneal astigmatism.
Figure 2:
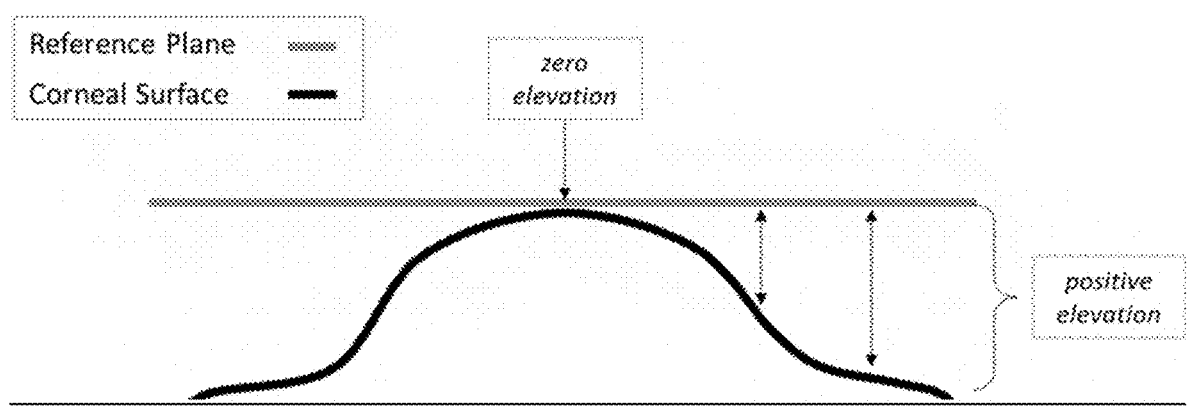
FIG. 2 presents a schematic view of measuring the elevation of different points on the corneal surface based on their distance from a reference plane tangent to the corneal apex.
Figure 3:
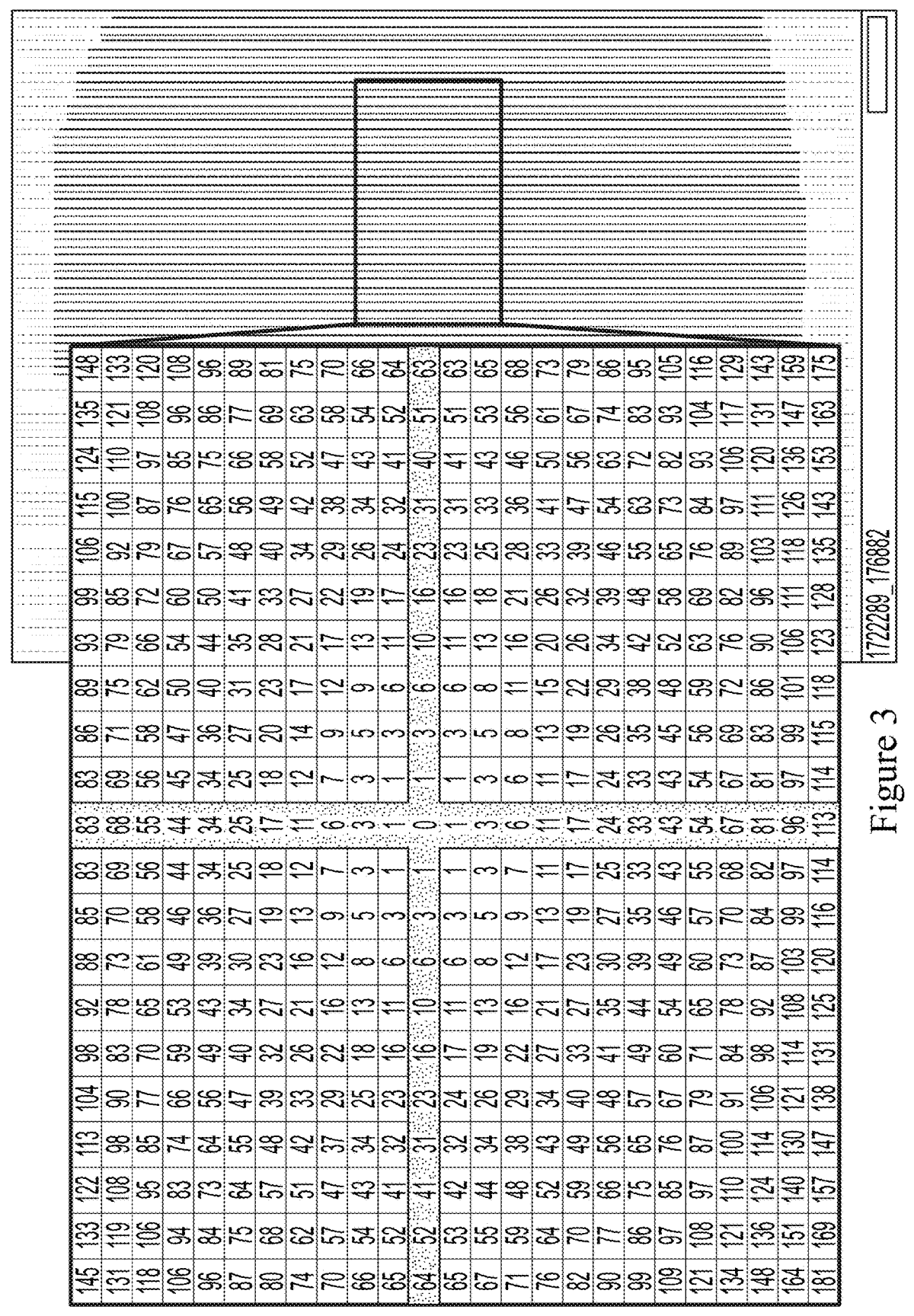
Figure 4:
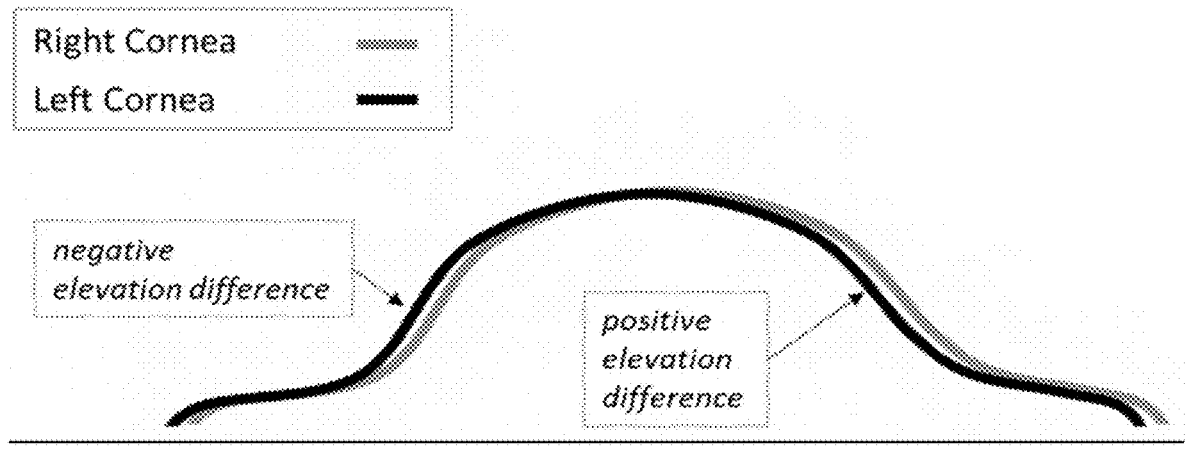
FIG. 4 is a schematic presentation of using the contralateral cornea as a reference for measuring elevation and assessing elevation symmetry between fellow eyes.

A dataset of 4613 adults (9000 imaging data files) was used in testing. The data for this project was provided by the Shahroud Eye Cohort Study, which is an observational cohort of adults between the ages of 40 and 64 years. For each participant/patient, both eyes were examined, and for each eye, there is one CSV file (FIG. 3) in which data are organized in coordinate points (from −7.0 mm to +7.0 mm with 0.1 mm increments), where the center of the cornea is at (0, 0). Data beyond the central 6 mm zone have little value (if any). For each measured characteristic, the data for each eye can be organized into a 141×141 matrix where the center of the cornea is in the center of the data frame. Since the topography patterns in fellow eyes are "mirror images," all left eye data are flipped 180 degrees around the Y axis. For each coordinate point, the inter-ocular difference in elevation is calculated (FIG. 4). Flattening this matrix provides a row of about 19,000 columns, 11,000 of which provide data for the central 6 mm zone of each eye.

Figure 5:
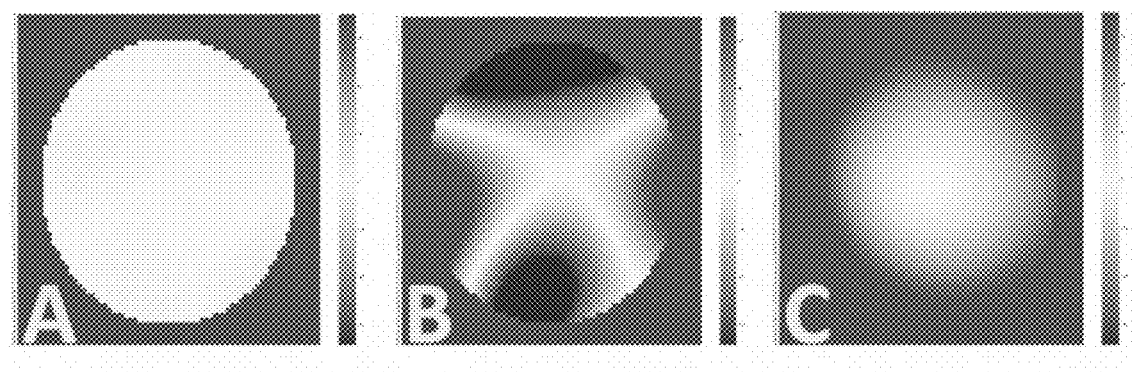
FIG. 5 shows common patterns in colormaps generated from anterior elevation fellow-eye difference matrices. The most common pattern (normal) was named "flat" (A) where there is minimal difference between anterior elevation measures of the two eyes. The next pattern (B) was named "four leaf", where the cornea in one eye is steeper in a certain meridian and flatter in the perpendicular meridian; this pattern is indicative of aniso-astigmatism or direct symmetry in the presence of astigmatism. The third pattern (C) was named "cone" which indicates one cornea is steeper than the other; this pattern is consistent with keratoconus.

Analyses on elevation data reviews that at any given point within the central 6-8 mm zone, the normal range of difference is generally under 10 microns (50%) and up to 30 microns (~90%). The most common pattern of elevation difference maps of the anterior corneal surface appear to be "flat" (FIG. 5A) which is consistent with normal symmetric eyes. Disease conditions show a round pattern with high difference values between the center and periphery of the difference map.

Existing tools and software can be implemented to increase accuracy and sensitivity. Pentacam raw elevation data is taken from fellow eyes to apply machine learning techniques. Python packages such as Pandas, NumPy, Matplotlib, and Seaborn, as well as various modules and codes, were used to process the raw elevation data of the entire anterior corneal surface, compute pancorneal elevation difference matrices, and create colormaps. The steps included data extraction, matching fellow-eye files, rotating the left eye matrix 180° around its Y axis, subtracting data on corresponding corneal point to create elevation differences matrices, exploratory analysis, data visualization, masking the matrix to access data points in five concentric central circles between 2.0 mm and 6.0 mm in diameter, and engineering features for clustering-based unsupervised machine learning. In data visualization, some of the common discernible patterns of interocular difference colormaps were "flat", "tilt", "cone", and "4-leaf", see FIG. 5 ("tilt" colormap not shown). The most common pattern is the flat pattern (FIG. 5A), which indicates that the fellow corneas fit well; this is the expected pattern when there is high symmetry and corneas are normal. In the 4-leaf pattern (FIG. 5B), one cornea is steeper in a given meridian and flatter in the perpendicular meridian compared to its fellow cornea, this pattern could be indicative of aniso-astigmatism or direct symmetry in the presence of astigmatism. In the cone pattern (FIG. 5C), one cornea is steeper than its fellow cornea, and the area between the two surfaces increases from the center to the periphery, this is consistent with keratoconus.

Machine learning techniques applied here are a combination of methods that effectively increase accuracy and sensitivity and can further be complemented with unsupervised archetypal models.

In the flattened matrix, the following was determined for the data within each row: count of valid data points, skew, absolute skew, kurtosis, mean, standard deviation of the mean, absolute mean (average of absolute means), median, absolute median, minimum, maximum, absolute maximum (the larger of maximum and absolute minimum), range, and central 95% range. The sums of negative and positive elevation difference values divided by 100 were used to calculate the negative and positive volumes, respectively, as well as the sum of the two volumes (Total Volume) and the absolute difference between the two volumes (Volume Difference) as a measure of intraindividual asymmetry.

Figure 6:
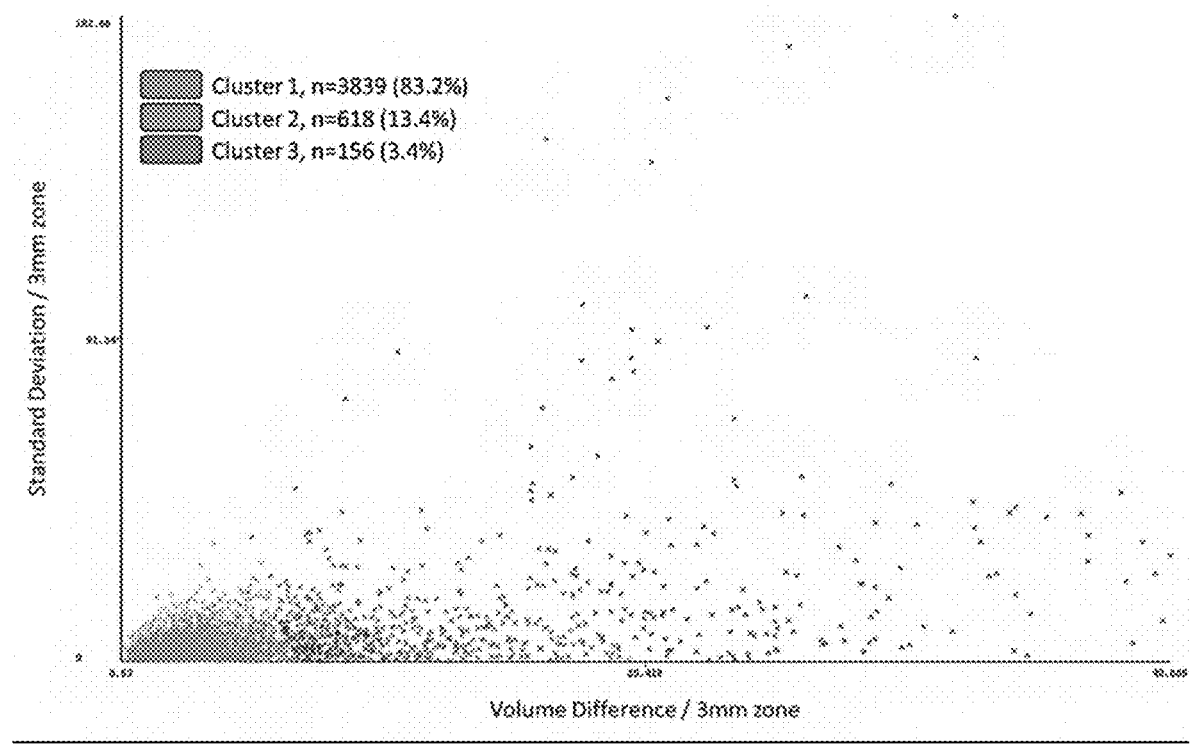
FIG. 6 shows the graphical results of Waikato Environment for Knowledge Analysis ("WEKA") validation of the invention using the simple k Means algorithm.
Figure 7:
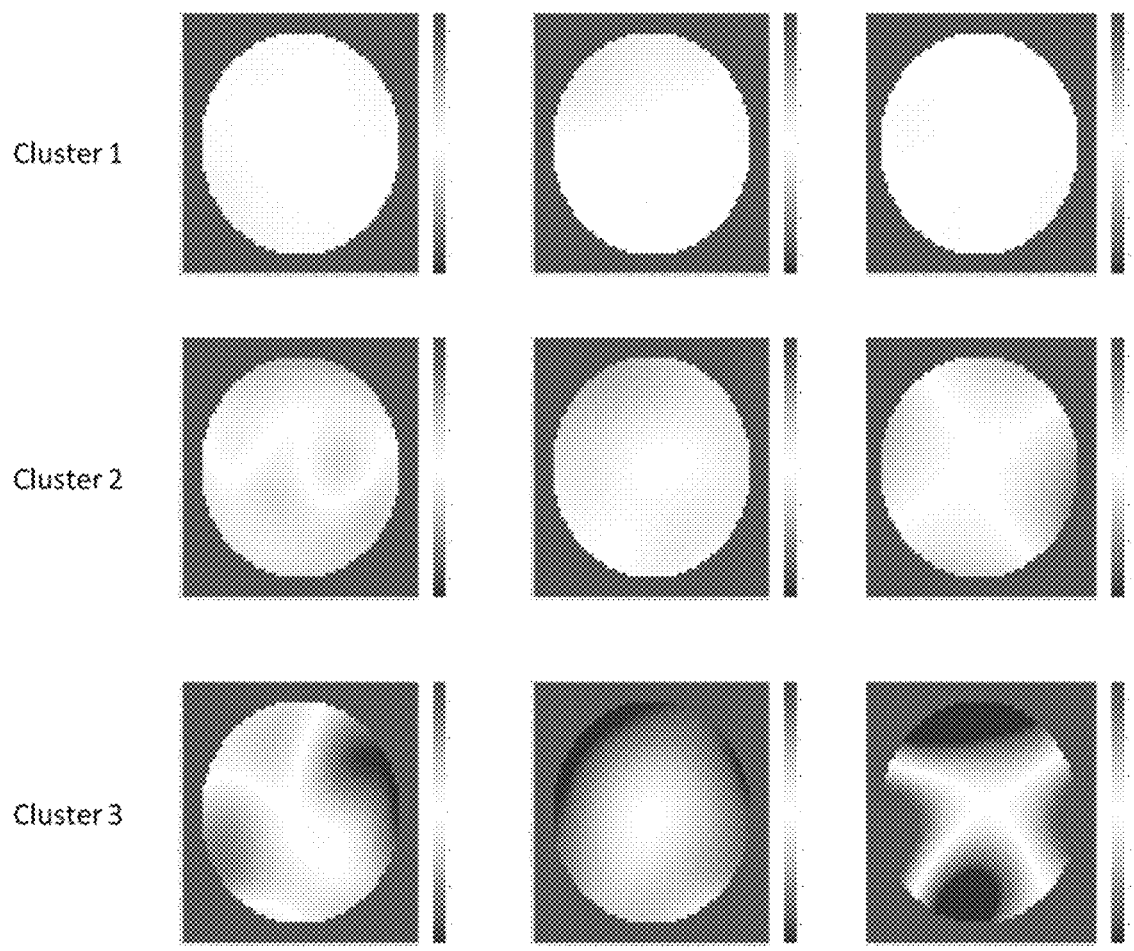
FIG. 7 illustrates sample 6.0 mm colormaps of three random cases from each of the three clusters based on Simple k Means and summary attributes including central 95% range of the 6.0 mm circle and the absolute mean, standard deviation of the mean, and volume difference of the central 3.0 mm circle. Cluster 1 corresponds with normal corneas where the colormap pattern is flat. Other patterns fall in cluster 2 and 3, although the degree of asymmetry is greater in the latter group.

Waikato Environment for Knowledge Analysis ("WEKA"), an open source data mining/machine learning software offering, was also used to validate the invention using the simple k Means (FIG. 6) clustering. Three clusters were generated, and mean interocular differences for measures of corneal thickness and keratometry in these clusters were in agreement with their corresponding groups. The number of datapoints in the 2.0, 3.0, 4.0, 5.0, and 6.0 mm circles were 317, 709, 1257, 1961, and 2821, respectively. Mean elevation difference in the 6.0 mm data of the entire sample was 0.20±15.6 and 99% of the data points were in the ±40 µm range. In 99% of individuals, the elevation differences in the central 3.0 mm were in the ±40 µm range. For each individual, the difference data in each circle was summarized into various statistics descriptive of central tendency and variability. The attributes using for clustering comprised of the central 95% range of the 6.0 mm circle data as well as the absolute mean, the standard deviation of the mean, and the volume difference attributes derived from the central 3.0 mm circle. Three clusters were generated (FIG. 6): 3839 (83.2%) in Cluster 1 as the normal group, 618 (13.4%) in Cluster 2 as the intermediate group, and 156 (3.4%) in Cluster 3 as the abnormal group. In the colormaps (FIG. 7), darker colors indicate greater interocular differences and are most noticeable in Cluster 3, as opposed to Cluster 1, which represented more normal groups, and Cluster 2, which represented an intermediate set of cases, showing lighter colors. Both the mean and the standard deviation (spread) of the summary statistics were significantly different between the three groups; values were lowest in Cluster 1 (best interocular elevation symmetry) and highest in Cluster 3 (least interocular elevation symmetry).

According to the invention, a basic set of inputs for a "refractive" software package may include data that leads to topography maps of the corneal surfaces, and output includes curvature maps, elevation maps, in multiple colors, and providing differential and comparative representation of various (including previous) examinations.

For image registration, initial concentric overlays may be provided to assist with geometric transformation for alignment of point sets. Computations of initial and subsequent exams may also be provided.

According to one embodiment, the invention may comprise software that is preferably integrated into a diagnostic device. By way of non-limiting example, the method of the invention may be accomplished using software integrated into the Oculus Pentacam which includes a rotating Scheimpflug camera to generate images of the anterior segment and which directly measures the height data (elevation) of both the anterior and posterior cornea. The device of the invention may then organize the elevation data for each cornea into a two-dimensional matrix where the center of the cornea is in the center of the data frame, rotate the data for a first eye 180 degrees around the Y axis relative to a second eye, apply image registration, subtract data on each corresponding corneal point, and generate an elevation difference matrix showing the degree of symmetry or asymmetry between the patient's left and right eye corneal topography.

The graphic user interface ("GUI") of the present invention may have options to display a coordinate system and concentric rings. Image registration will provide for 2-D adjustments, sliding on the X and Y axes, and output in the form of summary statistics may be provided for concentric 3 mm zone and 3-4, 4-5, and 5-6 mm rings.

It will be appreciated by those skilled in the art that changes could be made to the preferred embodiments described above without departing from the inventive concept thereof. It is understood, therefore, that this invention is not limited to the particular embodiments disclosed, but it is intended to cover modifications within the spirit and scope of the present invention as outlined in the present disclosure and defined according to the broadest reasonable reading of the claims that follow, read in light of the present specification.

The invention claimed is:

1. A method for early detection of eye disease comprising:
using a corneal topography device and integrated software to measure and store elevation data at a plurality of points on the patient's anterior corneal surfaces;
organize the elevation data for each cornea into a two-dimensional matrix where the center of the cornea is in the center of the data frame,
rotate the data for a first eye 180 degrees around the Y axis relative to a second eye, apply image registration,
subtract data on each corresponding corneal point, and
generate an elevation difference matrix showing the degree of symmetry or asymmetry between the patient's left and right eye corneal topography.

2. The method of claim 1, further comprising applying machine learning techniques to collected corneal topography data to develop and/or refine defined clusters for normal and various abnormal eye symmetries.

3. The method of claim 1, further comprising applying machine learning techniques to collected corneal topography data to improve image registration.

4. A device comprising:
a rotating Scheimpflug camera configured to measure the elevation of a patient's two anterior corneas sequentially or simultaneously;
a computer processor;
and non-transitory computer readable media including computer readable instructions, which, when executed by the computer processor, causes the device to
measure and store elevation data at a plurality of points on the patient's anterior corneal surfaces;
organize the elevation data for each cornea into a two-dimensional matrix where the center of the cornea is in the center of the data frame,
rotate the data for a first eye 180 degrees around the Y axis relative to a second eye,
subtract data on each corresponding corneal point, and
generate an elevation difference matrix showing the degree of symmetry or asymmetry between the patient's left and right eye corneal topography.

* * * * *